United States Patent
Forsyth (10) Patent No.: US 8,942,944 B2
(45) Date of Patent: Jan. 27, 2015

(54) SYSTEM AND METHOD FOR DYNAMICALLY MEASURING OXYGEN LEVELS

(75) Inventor: David E. Forsyth, Laguna Beach, CA (US)

(73) Assignee: Laguna Research, Inc., Laguna Beach, CA (US)

(*) Notice: Subject to any disclaimer, the term of this patent is extended or adjusted under 35 U.S.C. 154(b) by 747 days.

(21) Appl. No.: 13/231,661

(22) Filed: Sep. 13, 2011

(65) Prior Publication Data

US 2013/0066564 A1    Mar. 14, 2013

(51) Int. Cl.
G06F 19/00 (2011.01)
G06F 17/40 (2006.01)
G01N 33/00 (2006.01)
G01N 21/64 (2006.01)
G01N 21/27 (2006.01)

(52) U.S. Cl.
CPC .............. *G01N 21/643* (2013.01); *G06F 19/00* (2013.01); *G01N 33/00* (2013.01); *G06F 17/40* (2013.01); *G01N 21/274* (2013.01); *G01N 2021/6432* (2013.01); *G01N 2201/1211* (2013.01); *G01N 2201/1218* (2013.01); *G01N 2201/126* (2013.01); *G01N 2201/127* (2013.01); *G01N 2201/12746* (2013.01)
USPC ................ 702/104; 73/23.21; 702/1; 702/23; 702/24; 702/127; 702/187; 702/189; 708/200

(58) Field of Classification Search
CPC ........... G01D 7/00; G01D 9/00; G01D 21/00; G01N 31/00; G01N 31/22; G01N 31/223; G01N 33/00; G01N 33/0004; G01N 33/0006; G01N 33/0008; G01N 2033/00; G01N 2033/0004; G06F 11/00; G06F 11/30; G06F 11/32; G06F 11/34; G06F 15/00; G06F 15/16; G06F 17/00; G06F 17/10; G06F 17/40; G06F 19/00
USPC ......... 73/1.01, 1.02, 1.06, 23.2, 23.21, 432.1, 73/865.8, 866.3; 702/1, 22, 23, 24, 32, 85, 702/104, 127, 187, 189; 708/100, 105, 200
See application file for complete search history.

(56) References Cited

U.S. PATENT DOCUMENTS

| | | | | | |
|---|---|---|---|---|---|
| 2,422,129 | A | * | 6/1947 | Perley et al. | 436/136 |
| 2,448,111 | A | * | 8/1948 | Nicolai | 324/204 |
| 2,625,584 | A | * | 1/1953 | Kells et al. | 324/204 |
| 7,318,381 | B2 | * | 1/2008 | Arnold et al. | 110/185 |

(Continued)

FOREIGN PATENT DOCUMENTS

| GB | 1064871 A | * | 4/1967 |
|---|---|---|---|
| GB | 1081412 A | * | 8/1967 |

*Primary Examiner* — Edward Cosimano
(74) *Attorney, Agent, or Firm* — Bridget M. Hayden; Dorsey & Whitney LLP (57) ABSTRACT

An oxygen sensing system including an oxygen sensor, a microprocessor and one or more additional sensors for sensing parameters associated with the environment or with the oxygen sensor, accounts for one or more sensed conditions when calculating oxygen levels. The one or more sensors may sense conditions associated with environmental effects or effects of use that may cause the oxygen sensor to degrade over usage or over time. A baseline amplification and measurement circuit coupled to the oxygen sensor may enable the sensor to operate less frequently or for shorter periods of time, thereby increasing the life span, calibration hold time of the sensor, and reducing power requirements.

19 Claims, 7 Drawing Sheets

(56) References Cited

U.S. PATENT DOCUMENTS

2004/0137390 A1* 7/2004 Arnold et al. .................. 431/12
2006/0275718 A1* 12/2006 Arnold et al. .................. 431/13
2011/0314893 A1* 12/2011 Masui ............................ 73/1.06

* cited by examiner

SYSTEM AND METHOD FOR DYNAMICALLY MEASURING OXYGEN LEVELS

FIELD OF THE INVENTION

The present disclosure relates to oxygen sensing systems and methods. More particularly, the present disclosure relates to an oxygen sensing system that dynamically adjusts the oxygen level detected by an oxygen sensor based on changes in temperature, pressure and oxygen sensor parameters.

BACKGROUND

Oxygen sensors generally have short lifetimes such as less than 100 hours or have a high sensitivity to temperature variations (such as 0.01 PPO2/degree C. for fluorescent based sensors). For example, rebreathers are currently are limited to fuel cell based oxygen sensors and because these are chemical-based sensors, they require frequent calibrations, and have a limited lifetime thus making these sensors generally unreliable. Maximal oxygen consumption (VO2) measurements are generally limited to using CO2 sensors to infer oxygen levels, which can require significantly greater amounts of space and power than some types of oxygen sensors.

SUMMARY

Provided herein are oxygen sensing systems with increased lifetimes, greater stability and/or reliability. The oxygen sensing systems may have a high sensitivity to gasses that are tolerant to temperature swings and temperature variations over time. In some implementations, an oxygen sensing system determines an oxygen concentration level utilizing an oxygen sensor and a microprocessor that dynamically compensates for one or more of temperature, oxygen sensor use, oxygen sensor lifetime, and pressure to accurately calculate an oxygen level. In some implementations, the system may additionally utilize baseline amplification to determine oxygen levels. The system may also be configured for CO2 sensing utilizing sensed oxygen level data. The system may additionally use non-active sensing element baselines to filter environmental factors.

In some implementations, an oxygen sensing system includes an oxygen sensor that detects an oxygen level in an ambient gas environment; a temperature sensor that measures a temperature of the ambient gas environment; a microprocessor that receives the detected oxygen sensor output and the measured temperature; and a memory that stores calibrated temperature response data corresponding to a plurality of oxygen gas concentrations at a plurality of temperatures. The microprocessor dynamically adjusts the detected oxygen sensor output based on the measured temperature by comparing the detected oxygen sensor output with the calibrated temperature response data and determines a temperature independent oxygen level based on the comparison.

In other implementations, an oxygen sensing system includes oxygen sensor that detects an oxygen level in an ambient gas environment; a non-oxygen active environmental reference sensor that senses one or more environmental factors that is not responsive to ambient oxygen levels; a microprocessor that receives a signal from the oxygen sensor corresponding to the detected oxygen level and from the non-oxygen active environmental sensor corresponding to the one or more environmental factors; and a memory that stores data comprised of calibrated reference sensor response formulas corresponding to a plurality of non-active sensor outputs for one or more ambient environmental conditions and a corresponding output of the active oxygen sensor. The microprocessor calculates an environment independent oxygen level utilizing the signals from the oxygen sensor and the non-oxygen active environmental sensor as inputs for the stored calibration formulas.

In some implementations, a method for determining an oxygen level utilizing an oxygen sensing system involves detecting an oxygen level in an ambient gas environment utilizing an oxygen sensor; measuring a temperature of the ambient gas environment utilizing a temperature sensor; receiving the detected oxygen level and the measured temperature at a microprocessor coupled to the oxygen sensor and the temperature sensor; retrieving calibrated temperature response data corresponding to a plurality of oxygen gas concentrations at a plurality of temperatures stored in a memory utilizing the microprocessor; and dynamically adjusting the detected oxygen level based on the measured temperature by utilizing the microprocessor to compare the detected oxygen level with the calibrated temperature response data and to determine a temperature independent oxygen level based on the comparison.

In other implementations, a method for determining an oxygen level utilizing an oxygen sensing system includes detecting an oxygen level in an ambient gas environment utilizing an oxygen sensor; sensing one or more environmental factors that is not responsive to ambient oxygen levels utilizing a non-oxygen active environmental reference sensor; receiving at a microprocessor a signal from the oxygen sensor corresponding to the detected oxygen level and from the non-oxygen active environmental sensor corresponding to the one or more environmental factors; utilizing the microprocessor to retrieve from a memory data comprising calibrated reference sensor response formulas corresponding to a plurality of non-active sensor outputs for one or more ambient environmental conditions and a corresponding output of the active oxygen sensor; and utilizing the microprocessor to calculate an environment independent oxygen level utilizing the signals from the oxygen sensor and the non-oxygen active environmental sensor as inputs for the stored calibration formulas.

DETAILED DESCRIPTION

Provided herein are oxygen sensing systems and methods that employ microprocessor-based temperature and pressure calibration circuits for dynamically accounting for environmental factors and sensor parameters in an oxygen level calculation. Measurement circuits may be utilized in connection with the oxygen sensors to reduce the amount of time that a sensor requires to generate a measurement, for example, which may increase sensor life, time between calibrations, battery life, and accuracy. The oxygen sensor systems are generally utilized separately from non-dispersive infrared (NDIR) sensors, which typically detect the presence of a hydrocarbon based gas such as methane or gases such as carbon dioxide ($CO_2$). However, it will be appreciated that the systems and methods provided herein may utilize oxygen sensors in combination with NDIR-based systems.

According to certain implementations, the oxygen sensing system may include a fluorescence or phosphorescence quenching based oxygen sensor for detecting the presence of oxygen and a microprocessor for dynamically adjusting oxygen level calculation parameters utilizing data associated with changes in temperature, changes in pressure and changes in oxygen sensor parameters. The microprocessor thus generates calibration data by taking into account data associated with environmental or oxygen sensor parameters that may affect an oxygen sensor's ability to accurately detect oxygen levels.

Temperature Compensation

Generally, oxygen sensors are sensitive to temperature variations (such as 0.01 PPO2/degree C. for some types of fluorescence based sensors) and the oxygen sensor oxygen level outputs may be inaccurate due to temperature changes, which can not easily be passively. However, according to the implementation of FIG. 1, an oxygen sensing system 10 includes a temperature sensor 100 and a microprocessor 102 (e.g., a PIC24F64 GB106 microprocessor) to account for temperature variations in the environment in which the oxygen sensor 107 is located.

Figure 1:
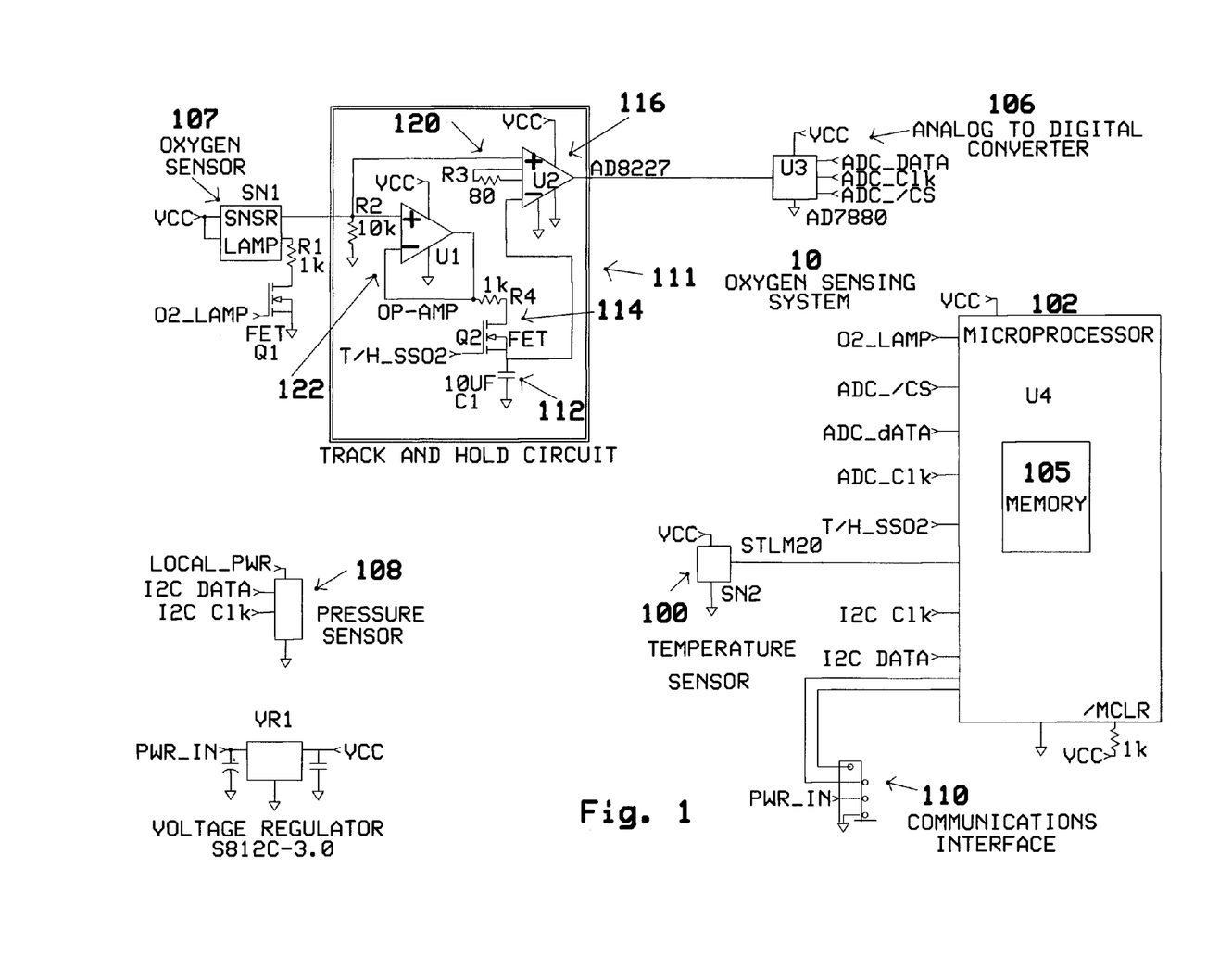
FIG. 1 is a circuit diagram, according to certain embodiments for an oxygen sensor element with a track-and-hold baseline measurement circuit.

In this preferred implementation, the temperature sensor 100 is placed in proximity to the oxygen sensor 107. The microprocessor 102 may measure the temperature in relation to readings from the oxygen sensor 107 and may adjust the oxygen level outputs based on the temperature measured by the temperature sensor 100.

According to certain embodiments, the microprocessor 102 may generate calibration data using a set of oxygen output readings from the oxygen sensor 107, which may be collected from a plurality of temperatures over a known range of oxygen levels. The calibration data may be stored in the memory internal to the microprocessor 102 as a calibration table. For example, the microprocessor 102 may be configured to implement a calibration technique that applies the temperature data collected from the oxygen sensing element 107 using a multivariate curve fitting approach according to standard data analysis techniques, such as a two-dimensional multiple linear regression. The calibration technique may establish the calibration formula and the variables to fit that formula to the observed behavior of any specific sensing element to the observed calibration temperature and oxygen level data.

Figure 2:
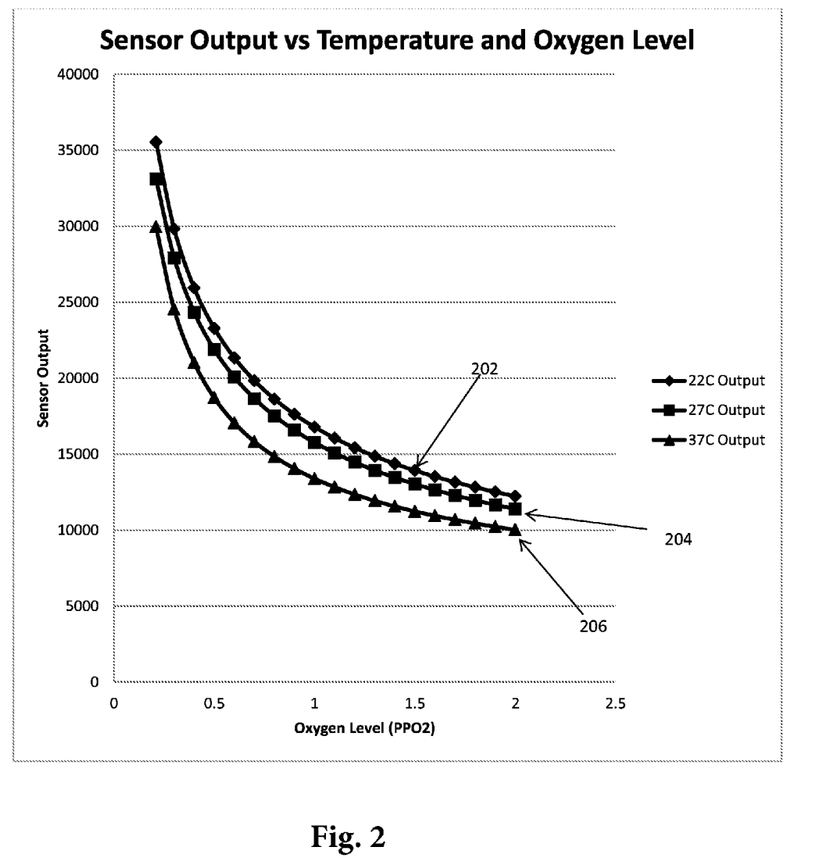
FIG. 2 is a graph of an output of an oxygen sensing element versus gas concentration and temperature.

FIG. 2 shows a set of temperature and oxygen calibration data collected from an oxygen sensor 107 generating an oxygen response curve for the temperature points of 22 degrees Celsius (oxygen response curve 202), 27 degrees Celsius (oxygen response curve 204), and 37 degrees Celsius (oxygen response curve 206). The individual data points form the constant temperature curves when analyzed together using a method such as least squares regression, and based on the constant temperature curves, parameters may be determined to enable the microprocessor 102 to maintain a calibrated output given the inputs of sensor output and ambient temperature. Data may be gathered with similar results following such methods as maintaining constant oxygen rather than constant temperature with similar calibration means. The following formula is an example of the type of equation that may be generated and stored in the internal microprocessor 102 memory and utilized by the microprocessor 102 for determining a calibrated multivariate response from a non-linear sensor element by means of a regression analysis. Such analysis may yield multiple equations of varying fit and complexity, which are then selected from according to varying system design parameters such as processor speed, memory size, accuracy requirements, and so on. As an example, such an analysis may yield a sufficient fit to an equation similar in form to $$f(O2, Tmprtr) = a + (b*TmptrSnsr + c)\hat{\ }d*(e*O2Snsr + f)\hat{\ }g$$

where the fitted parameters may be determined to be similar to:
a=−7.6271743947546142E−02;
b=−1.3076104322922939E+02;
c=6.4569707165102627E+03;
d=4.0515000212857388E−01
e=1.0062688944358265E−03;
f=−5.6440192333025463E+00;
g=−1.3528634961221531E+00;
and be calculated in a language such as C as follows:

PPO2=a+pow(d*sgs_Tmprtr_Snsr_._f_Temperature_C+f,b)*pow(g*f_SSO2_Raw_Ave+h,c);

In this manner, oxygen sensors such as a fluorescence or phosphorescence quenching based sensor (SN1), that may exhibit temperature sensitivity unsuitable for standard analog compensation techniques may be used in combination with microprocessor 102 coupled to the temperature sensor 100 to produce a linear output.

An additional benefit to such techniques is that for some types of oxygen sensors, such as a fluorescence or phosphorescence quenching based sensor (SN1), the output decay or change that would normally occur over time or use, may remain sufficiently linear for standard straight line single or two point calibration techniques to be applied, which may increase the general ease of calibrating the oxygen sensing system during the ongoing use of the sensor system.

In some implementations, the oxygen sensing system may perform calibration processes or may store calibrated data having been generated by the following steps: sampling gases across a range of oxygen concentrations at a number of ambient gas temperatures; collecting oxygen sensor outputs for the sampled oxygen concentrations at the differing ambient gas temperatures; measuring temperature sensor outputs for the plurality of ambient gas temperatures; determining a best fit calibration equation by approximating a calibration curve with a multi-variant fit based on the oxygen sensor outputs and oxygen concentrations and ambient gas temperatures related to the oxygen sensor output; and computing a set of fitted coefficients corresponding to the calibration curve based on the measured oxygen sensor outputs and the related oxygen concentrations and ambient gas temperatures. Using this calibration process or using data generated according to this process, the microprocessor calculates the oxygen concentration in the ambient gas environment by applying ambient gas temperature data and oxygen sensor outputs as variables to the calibrated oxygen concentration data received from the memory.

Oxygen Sensor Lifetime Compensation

Figure 3:
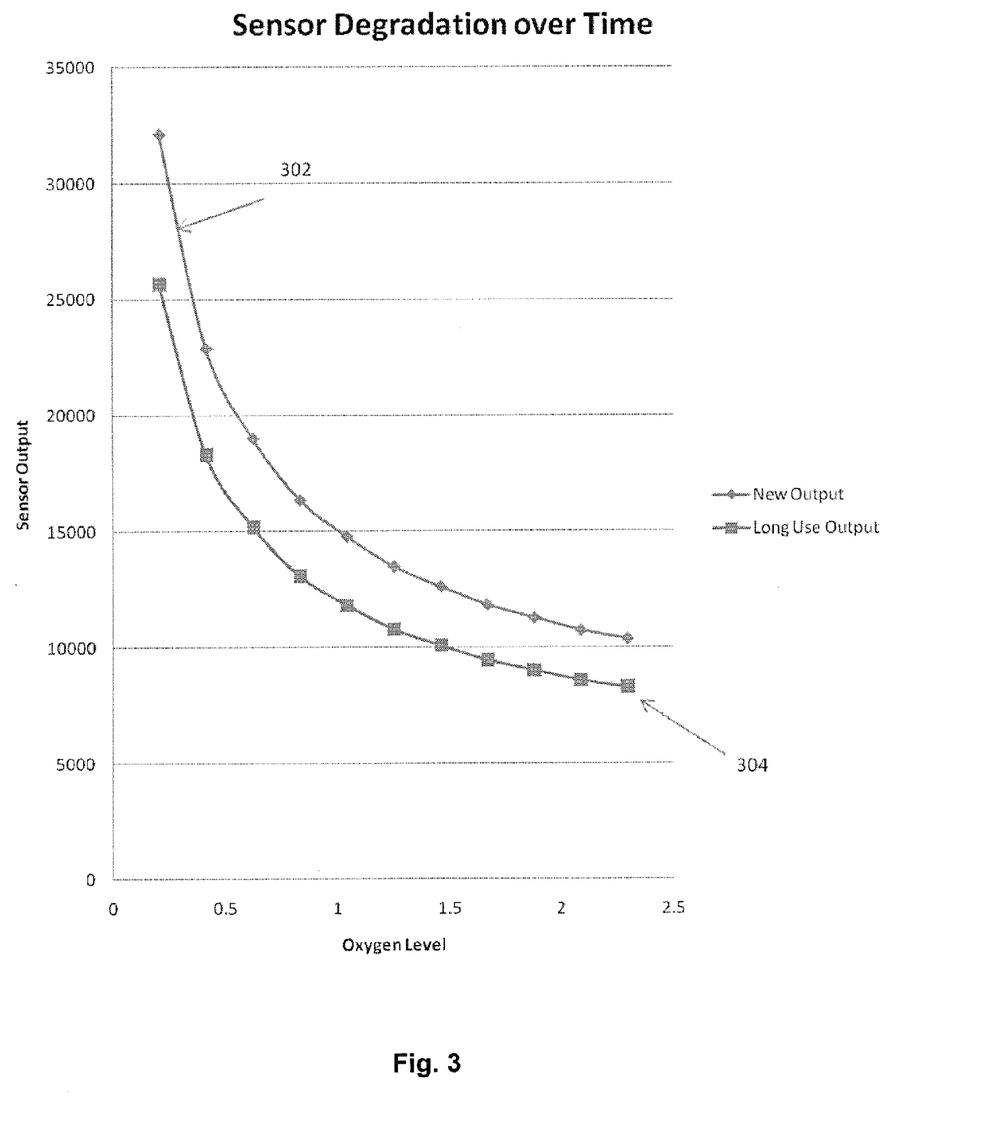
FIG. 3 is graph oxygen sensing element output for oxygen levels versus use time.

Over time, oxygen sensors may change its response to oxygen relative to both environmental parameters as well as to the oxygen level itself, and thus become less accurate. More specifically, the sensing capabilities of the oxygen sensor may degrade over its time of use and/or may degrade based on the age of the sensor. For example, FIG. 3 is graph of an oxygen sensor output for oxygen levels versus time. Line 302 represents a stronger signal output such as might be found in a recently produced and calibrated sensor. Line 304 represents the same sensor after some period of use. This degradation may be characterized by tracking the time and conditions of use or general age, and the formulas representing that change relative to those conditions may be stored in the microprocessor memory to allow calculations to be made to account for the age and/or use of the sensor when sensing oxygen levels utilizing the oxygen sensor.

In certain implementations, the microprocessor 102 may be programmed to retrieve data corresponding to general oxygen sensor response changes according to age or use-time of the oxygen sensor 107. For example, the age of the oxygen sensor 107 may be determined to by an accumulated time of use, such as by a use timer, which may be stored within the memory 105. In some implementations, the level of oxygen exposure over time is stored within the memory 105. The microprocessor 102 may retrieve the stored information related to the use or age of the oxygen sensor to identify the aging parameters and adjust the calibration data parameters according to the determined age/exposure of the sensor device. In this way, longer term sensor output stability may be maintained. This may decrease the frequency or severity of calibration requirements. Accordingly, the microprocessor 102 may take into account one or more use or aging parameters in calculating calibration parameters, such as the calibration techniques relating to multivariate curve fitting techniques.

Calibrated Pressure Response

In some implementations, oxygen sensing systems may use pressure sensors or may receive information related to sensed pressure of the atmosphere in which the oxygen sensor is located in order to account for variations in pressure. These pressure sensors may be useful in combination oxygen sensors affected by changes in pressure, such as in diving applications, e.g., oxygen sensing systems incorporated in rebreathers.

In this implementation, a pressure sensor 108 may be calibrated to ensure accurate oxygen sensor outputs. For example, the pressure sensor 108 may be incorporated into the oxygen sensor 107. In addition or alternatively, ambient pressure sensor data may be received remotely by the microprocessor 102 via a communications interface 110 as shown in FIG. 1. This data may be incorporated in a similar manner as previously discussed but substituting pressure calibration for the temperature calibration using techniques such as an n-dimensional multiple linear regression formula and standard statistical analysis techniques to determine appropriate formula and parameters.

Oxygen Sensor Baseline Amplifier Circuit

A baseline amplifier circuit may receive the output from the oxygen sensor for creating a measurable signal change relative to a baseline output level. The baseline circuit compares an active (oxygen level related) signal from the oxygen sensor against a baseline voltage level (an output not related to oxygen level) to allow a non-frequency based measurement to be generated using the oxygen sensor's signal. The baseline circuit utilizes a baseline amplifier, described below, and only the portion of the signal with the relevant information is amplified rather than any non-relevant offset level. This allows for a higher level of signal amplification as well as short sensing element powered on times (since it is not a capacitively coupled and frequency dependent system), which may be useful in the oxygen sensing system 10, for example when it is desired to increase the lifetime of the sensor by decreasing the active measurement time. Additionally, it may also be useful to take very short measurements in order to take many measurements in a short period of time in order to increase the accuracy or resolution of the output of the oxygen sensor system 10.

According to certain implementations, a baseline amplifier circuit may be configured as a track and hold circuit 111 shown in FIG. 1 By amplifying an active signal against the baseline, small differences in DC signal voltage levels may be differentially amplified without the use of capacitively coupled amplifiers and thus achieved in very small amounts of time without the need for 50% duty cycle measurements, which are generally necessary for many capacitively based systems.

For example, a track and hold circuit may be used in an oxygen sensor system in order to establish a signal baseline from a non-oxygen responsive period of a sensor output signal. This non-responsive period in the embodiment shown in FIG. 1 may be generated by microprocessor 102 using one or more control signals, which function to control the active output of the oxygen sensor 107.

The track and hold circuit may include components such as a capacitor 112 for storing an electric charge, a FET switch 114 that switches the baseline voltage to the capacitor, and an amplifier 116 that amplifies the difference between the baseline voltage and the active voltage output corresponding to the oxygen level sensed by the oxygen sensor. By using a baseline amplifier such as a track and hold circuit 111, only the portion of the signal with the relevant information is amplified rather than any non-relevant offset level. This allows for a higher level of signal amplification as well as very short sensing element powered on times or the ability to make many measurements in a short amount of time such as may be necessary for increased accuracy or resolution or response time. In addition, in some types of oxygen sensors, the null or non-active component of the sensor output is sensitive to non-relevant factors such as light, temperature, voltage levels, or pressure as examples. By using a baseline amplification approach, it may be possible to eliminate much of the effect of various factors that may adversely affect calibration.

With particular reference to FIG. 1, the track and hold circuit 111 FET switch 114 may be provided as a common NFET (Q2: N-type ND3332), the capacitor 112 may be provided as a voltage-holding capacitor (C1:10uf) and the amplifier 116 may be provided as a high gain single stage amplifier (U2 ADC8720) with a gain of approximately 1000 as set by the gain resistor 120 (R3=80 ohms). A low-offset opamp 122 (U1, OPA2333) on the input of the baseline FET 114 may buffer the charging current requirements of the hold capacitor from the actual measured signal. This may provide an improved baseline voltage on the holding capacitor 112. The holding capacitor 112 may be sufficiently large and may have a low enough leakage as to hold the required baseline voltage for the relatively long periods of time (up to several hundred microseconds) as it may take the microprocessor 102 (U4, a Microchip PIC24FJ64 GB102) and Analog-to-Digital-Converter 106 (U3, an Analog Devices AD7880) to measurement of the gas concentration signal levels to enable full range amplification.

Providing a baseline circuit for the oxygen sensors, according to certain embodiments, may replace the capacitive coupled, frequency tuned amplifier circuits commonly used in applications with high levels of voltage offset relative to the active signal. In other embodiments, a baseline voltage may be captured by a direct capture measurement via an analog to digital converter and the determination of difference between active and baseline voltages is captured and analyzed mathematically within a microprocessor.

Figure 4:
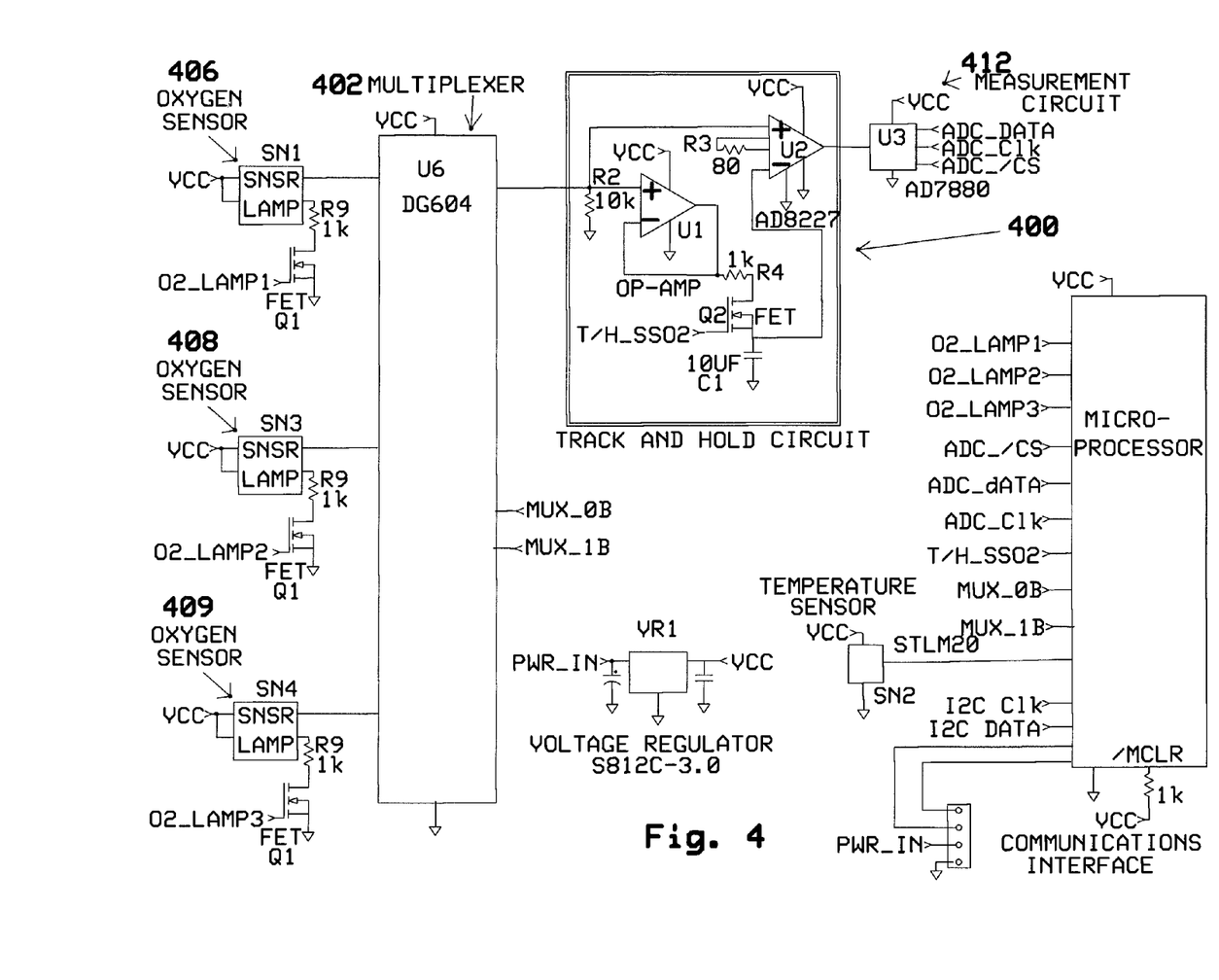
FIG. 4 is a circuit diagram, according to certain embodiments, for multiple sensors on a common baseline measurement circuit.

With reference to FIG. 4, the application of a track and hold circuit 400, with minor modifications such as an input multiplexer 402, may be used to measure other sensor signals that, in some cases, may encounter DC biases. Thus, certain embodiments allow for the inclusion of additional sensor signals such as multiple oxygen sensing elements 406, 408, 410 using a track and hold circuit 400 and measurement circuit 412, both because of the nature of track and hold circuit 400 and also because it is not inherently frequency based and so may be switched between differing signal inputs and used regardless of whether the measured signal has a large offset or no offset. As a result, significant size, cost, and power savings may be realized for multiple sensor applications due to the ability of the track and hold circuit 400 to accommodate multiple sensors or sensing elements with common measurement electronics as shown in FIG. 4. Multiple sensing elements used with the standard approach of capacitively coupled, frequency tuned amplifiers typically must replicate the entire amplification circuitry for each sensor element. In some examples, the track and hold circuit 400 may be a common baseline amplifier.

Calculated CO2 Levels

In addition, some oxygen sensors may be configured to sense relatively low oxygen levels, such as the oxygen levels of ambient air. Generally, such sensors have limited usefulness in determining carbon dioxide (CO2) levels required for instance for capnography measurements due to the relatively small levels of CO2 compared to oxygen and in some cases due to the sensor being highly temperature sensitive. That is, CO2 measurements are difficult in medical environments where the temperature varies due to expired or inspired/expired breath.

According to the implementations provided herein, some types of oxygen sensing elements, such as a fluorescence or phosphorescence quenching based element 107 illustrated in FIG. 1, may exhibit sufficient resolution at low levels of oxygen, such as found in air, to detect CO2 levels. This is because higher levels of oxygen sensing system stability, resolution, calibration, and sensor lifetime may be achieved utilizing the implementations described above, and thus the oxygen sensor utilized in the oxygen sensor system, such as a fluorescence or phosphorescence quenching oxygen sensor, offers the ability to measure CO2 levels.

According to certain implementations, the microprocessor 102 may be configured to calculate oxygen levels based on calibration data such that the change of oxygen levels from either an input or a recorded nominal baseline is used to infer ambient CO2 levels by relating a detected change in oxygen levels to the ambient CO2 level by means of subtracting the baseline oxygen level (such as an inspired breath level) from the expired oxygen level. As one example, this would allow CO2 levels to be calculated in gases in which the exact level of oxygen is not known such as a medical environment with anesthetic gases added to the breathing mix. The added functionality of measuring CO2 levels may be useful in determining changes in ambient CO2 levels due to biological processes.

Non-oxygen Sensing Environmental Offset Element

Figure 5:
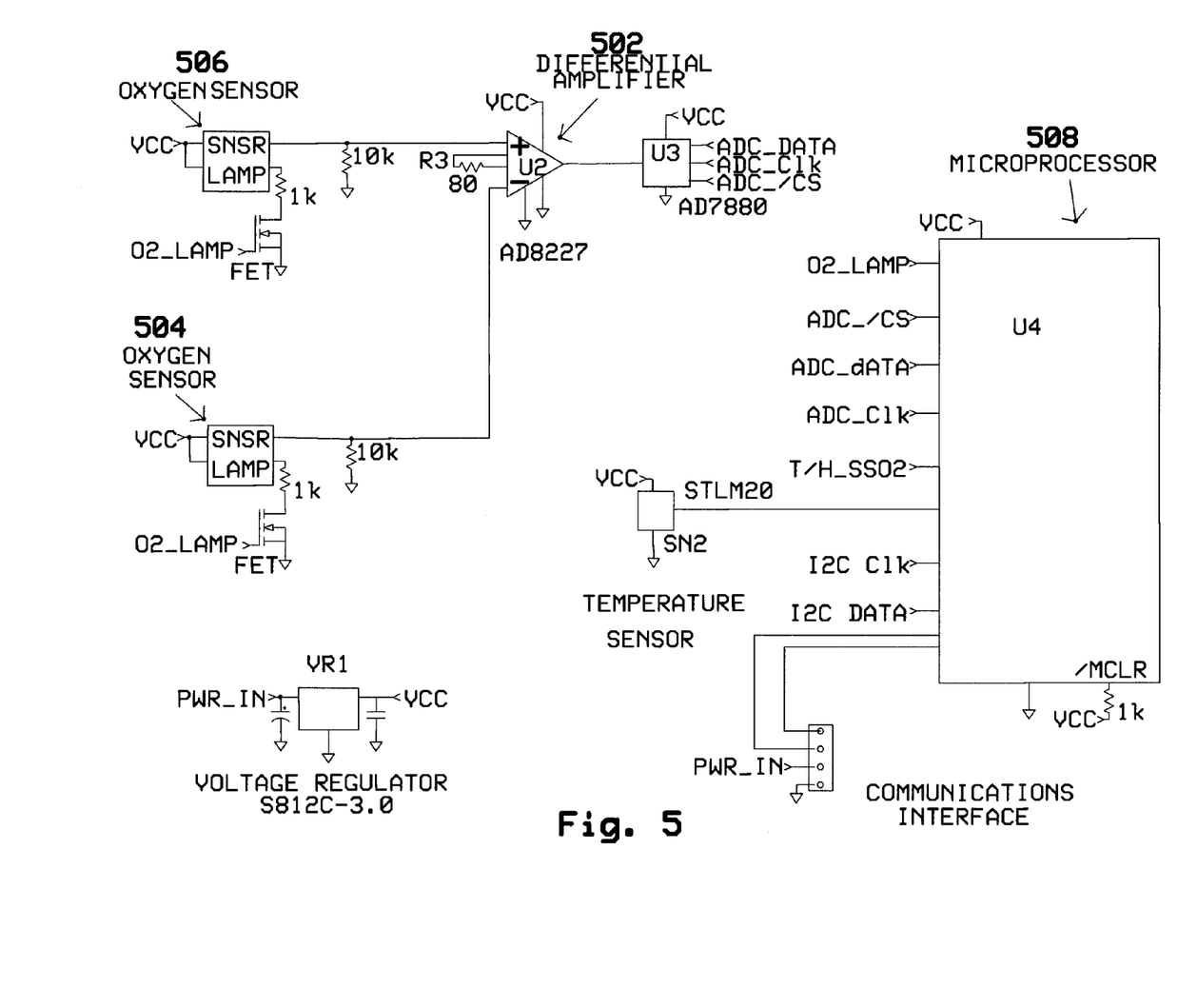
FIG. 5 is a circuit diagram, according to certain embodiments, for a single oxygen sensor element with a non-oxygen active sensing element baseline measurement circuit.

Some oxygen sensors may be treated or modified to inhibit the ability to respond to oxygen level changes, while maintaining sensitivity to other types of secondary changes in the environment of the sensing element such as temperature, pressure, voltage, light, and so on. For example, an oxygen sensor may utilize fluorescence or phosphorescence quenching with an oxygen-proof, optically clear sealant applied to the sensing surface. The non-oxygen active oxygen sensor 504 may generate changes in baseline output levels that may be used to compensate for baseline changes using a differential amplifier 502, which differentially amplifies signals from the non-oxygen active element 504 and the active oxygen sensing element 506 with a resultant reduction in circuitry as shown in FIG. 5. In certain embodiments, calibration techniques as demonstrated above involving the use of multi-variant curve and parameter fitting techniques may be employed to achieve a calibrated response to varying levels of sensed oxygen.

In use, the active oxygen sensing element 506 may detect an oxygen level in an ambient gas environment, the non-oxygen active sensing element 504 may sense one or more of the secondary changes in the environment, and each of the sensing elements 504 and 506 may generate a voltage output. The voltage output produced by the active oxygen sensing element 506 may be based on the oxygen level as well as the secondary environmental factors, while the voltage output produced by the non-oxygen active sensing element 504 may be based on the secondary environmental factors and not the oxygen level. A microprocessor 508 may compare the voltage outputs to determine the actual oxygen level. In some implementations, the microprocessor 508 is communicatively coupled with a memory that stores calibrated reference sensor response data that includes non-oxygen active sensor 504 outputs for one or more ambient environmental conditions and a corresponding output of the active oxygen sensing element 506. The microprocessor 508 may calculate an environment independent oxygen level utilizing the signals from the oxygen sensor and the non-oxygen active environmental sensor as inputs for the stored calibration formulas.

It will be appreciated that the oxygen sensing systems of FIGS. 1 and 5 may include additional components and that at least some aspects of each system may be used interchangeably with the other.

Oxygen Sensing Processes

Figure 6:
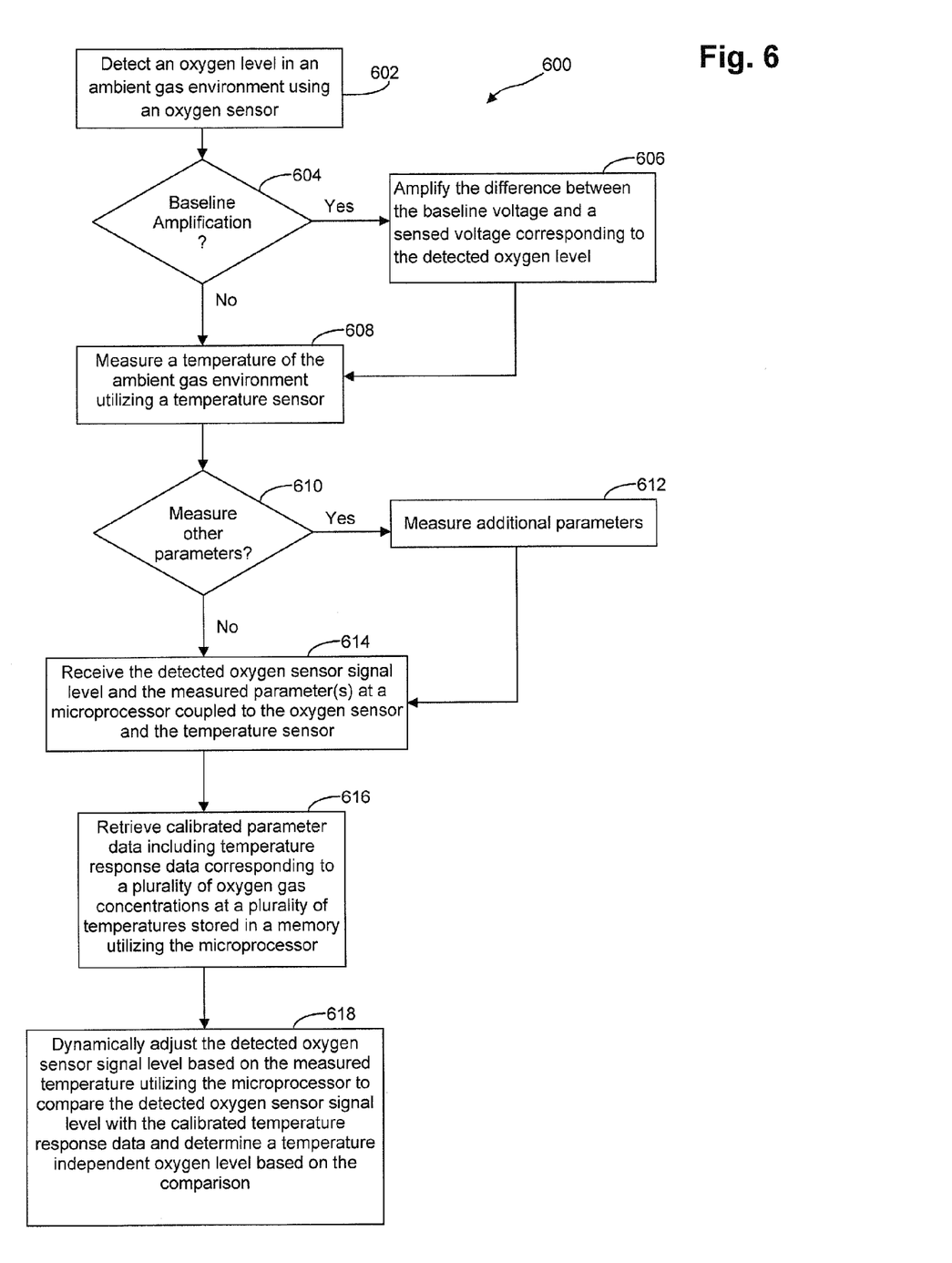
FIG. 6 is a flow diagram of a method for dynamically adjusting an oxygen level detected by an oxygen sensor based on changes in temperature, pressure and oxygen sensor parameters utilizing the oxygen sensing system of FIG. 1.

Turning to FIG. 6, illustrated is a flow diagram for a method 600 for measuring an oxygen level by dynamically adjusting the oxygen level detected by an oxygen sensor based on changes in one or more of temperature, pressure and oxygen sensor parameters utilizing the oxygen sensing system 10 of FIG. 1. The method begins at block 602 where an oxygen level is sensed in an ambient gas environment using an oxygen sensor and a corresponding output signal is produced. The flow proceeds to block 604 where the processor determines whether baseline amplification is used in connection with sensor output level. If so, the flow proceeds to block 606 where the difference between the baseline voltage and a sensed voltage corresponding to the detected oxygen level is amplified, and the flow then proceeds to block 608 where the temperature of the ambient gas environment is measured using a temperature sensor. If baseline amplification is not used, the flow proceeds to block 608.

Following block 608, the flow proceeds to block 610 where the microprocessor 102 determines whether other parameters are to be measured. The additional parameters may include pressure, oxygen sensor use, oxygen sensor lifetime, as well as other parameters that may affect the oxygen sensor's ability to accurately detect oxygen levels. If additional parameters are measured, the flow proceeds to block 612 where the additional parameter measurement data is obtained using the microprocessor 102, which may be communicatively coupled to one or more measuring circuits or measuring devices, e.g., pressure sensor, duration clock, real time clock, and so on. If additional parameter data is not measured, the flow proceeds to block 614. At block 614, the microprocessor 102 receives the detected oxygen sensor output data from the oxygen sensor, the detected temperature data from the temperature sensor and any other parameter data from the measuring devices.

The flow then proceeds to block 616 where the microprocessor 102 retrieves calibrated parameter data including temperature response data corresponding to a plurality of oxygen gas concentrations at a plurality of temperatures stored in a memory internal to the microprocessor 102. It will be appreciated that the calibrated parameter data may be generated based on additional parameter data for parameters that may affect the oxygen sensor's ability to accurately detect oxygen levels. The flow then proceeds to block 618 where the microprocessor 102 dynamically adjusts the detected oxygen sensor signal level based on the measured temperature by comparing the detected oxygen sensor signal level with the calibrated temperature response data and determining a temperature independent oxygen level based on the comparison.

Figure 7:
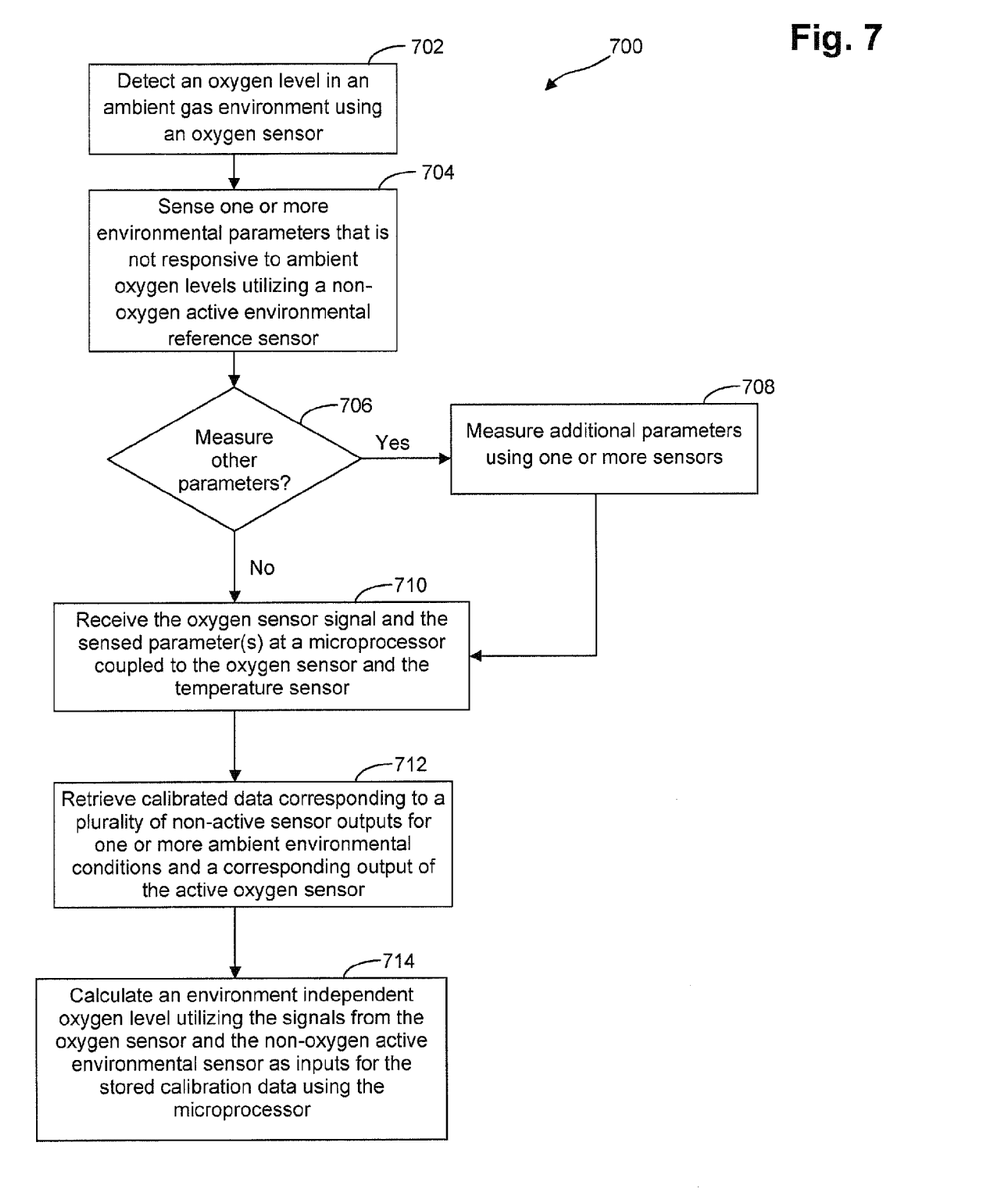
FIG. 7 is a flow diagram of a method for determining an oxygen level detected by an oxygen sensor based on a comparison of the signal produced by the oxygen sensor with a non-oxygen active environmental sensor utilizing the oxygen sensing system of FIG. 5.

FIG. 7 illustrates a flow diagram for a method 700 for determining an oxygen level detected by an oxygen sensor based on a comparison of the signal produced by the oxygen sensor with a non-oxygen active environmental sensor. The method may be performed by the oxygen sensing system of FIG. 5. The method begins at block 702 where an oxygen level in an ambient gas environment is detected using an oxygen sensor. The flow proceeds to block 704 where one or more environmental parameters such as temperature, pressure, voltage, and light, and other parameters that are not responsive to ambient oxygen levels, are sensed using a non-oxygen active environmental sensor. The flow proceeds to block 706 where the microprocessor 508 determines whether other parameters are to be measured. If "yes" the flow continues to block 708 where additional parameters are measured by one or more sensors. From block 706 if "no " (no other parameters are to be measured),or block 708, the flow proceeds to block 710 where signals associated with the detected oxygen level and the sensed one or more sensed parameters (e.g., environmental parameters and additional parameters) are received by the microprocessor 508. The flow continues to block 712 where the microprocessor retrieves calibrated data from memory, which may correspond to a plurality of non-active sensor outputs for one or more ambient environmental conditions and a corresponding output of the active oxygen sensor. The flow then proceeds to block 714 where the microprocessor calculates an environment independent oxygen level utilizing the signals from the oxygen sensor and the non-oxygen active environmental sensor as inputs for the stored calibration data.

It will be appreciated that although the method 600 of FIG. 6 utilizes the oxygen sensing system of FIG. 1 and the method 700 of FIG. 7 utilizes the oxygen sensing system of FIG. 5, the flow diagrams of FIGS. 6 and 7 may include additional block and that at least some aspects of each method 600, 700 may be used interchangeably with the other.

Additional Implementations and Applications

In some implementations, the oxygen sensing system may be communicatively coupled to a display system and may transmit the temperature independent oxygen level to the display system for viewing by a user. In some implementations, the oxygen sensing system may be integrated within devices that require oxygen sensing functions, such as oxygen regulators.

A number of improved oxygen sensing applications are possible based on the various embodiments of the present disclosure. The benefits may include an increase in useful sensor life due to the shortened measurement times, lower power requirements (again due to shortened measurement times), greater temperature stability (due to active, microprocessor based temperature compensation), greater response speed, accuracy, and resolution each of which may be possible due to shorter measurement times and the concurrent ability to take many measurements in shorter amounts of time.

The aforementioned benefits provided by the oxygen sensing systems provided herein may enable the system to replace traditional oxygen sensing systems such as fuel cell sensors, including those used in firefighting personal gas sensors. The fuel cell sensors generally require frequent calibration and regularly replacement at significant cost. However, the oxygen sensing systems provided herein, such as those utilizing a fluorescence based sensor, may last longer and may be more calibration stable as well as be small enough to make additional uses such as embedded in a filtered air face mask practical.

In another example, the oxygen sensing systems may be useful for measuring oxygen consumption levels during exercise and in medical applications. Oxygen sensors typically do not have the sensitivity to accurately determine the amount consumed in a breath and those that may have that sensitivity may be too temperature sensitive or have impractical lifetimes such that other means of determining oxygen consumption must be used. Some implementations of the present disclosure may allow an oxygen sensor such as fluorescence based sensor to be stable enough in temperature and have a sufficient accuracy and lifetime to sufficiently measure the change in oxygen levels in a breath and thereby determine oxygen consumption. These and other applications of use may be provided by the benefits discussed above.

While the embodiments herein provide memory integrated within the microprocessors, it will be appreciated that the microprocessor may be operatively coupled to other data storage units storing calibration data, temperature data, pressure data, oxygen sensor data, and the like. Such data storage units may include non-transitory storage media, which may take the form of, but is not limited to, a magnetic storage medium; optical storage medium; magneto-optical storage medium; read only memory; random access memory; erasable programmable memory; flash memory; and so on.

Although the various embodiments of the present disclosure have been described with reference to preferred embodiments, persons skilled in the art will recognize that changes may be made in form and detail without departing from the spirit and scope of the present disclosure.

What is claimed is:

1. An oxygen sensing system, the system comprising:
    an oxygen sensor for detecting an oxygen level in an ambient gas environment;
    a temperature sensor for measuring a temperature of the ambient gas environment;
    a microprocessor coupled to the oxygen sensor and the temperature sensor for receiving the detected oxygen sensor output and the measured temperature; and a memory within the microprocessor for storing calibrated temperature response data corresponding to a plurality of oxygen gas concentrations at a plurality of temperatures;

wherein the microprocessor dynamically adjusts the detected oxygen sensor output based on the measured temperature by comparing the detected oxygen sensor output with the calibrated temperature response data and determines a temperature independent oxygen level based on the comparison.

2. The system of claim 1, further comprising a baseline amplifier comprising a track and hold configured differential amplifier, comprising:

a capacitor;

a switch for controlling a charge delivered to the capacitor, wherein the capacitor is charged with a baseline voltage, and upon opening the switch, the capacitor retains the baseline voltage; and an amplifier, wherein the amplifier amplifies a difference between the baseline voltage and a sensed voltage corresponding to the detected oxygen sensor output.

3. The system of claim 1, wherein the stored calibration data is generated by:

sampling gases at a plurality of oxygen concentrations at a plurality of ambient gas temperatures;

measuring oxygen sensor outputs of the sampled oxygen concentrations at the plurality of the related ambient gas temperatures;

measuring temperature sensor outputs for the plurality of ambient gas temperatures;

determining a best fit calibration equation by approximating a calibration curve with a multi-variant fit based on the oxygen sensor outputs and oxygen concentrations and ambient gas temperatures related to the oxygen sensor output; and computing a set of fitted coefficients corresponding to the calibration curve based on the measured oxygen sensor outputs and the related oxygen concentrations and ambient gas temperatures; and wherein the microprocessor receives data from the oxygen sensor associated with the measured oxygen outputs and data from the temperature sensor comprising a measured ambient gas temperature, and calculates the oxygen concentration by applying the ambient gas temperature data and oxygen sensor outputs as variables to the calibrated oxygen concentration data received from the memory.

4. The system of claim 1, further comprising a pressure sensor for detecting an ambient gas pressure, wherein the stored calibration data is generated by:

sampling gases at a plurality of oxygen concentrations at a plurality of ambient gas pressures;

measuring oxygen sensor outputs of the sampled oxygen concentrations at the plurality of the related ambient gas pressures;

determining a best fit calibration equation by approximating a calibration curve with a multi-variant fit based on the oxygen sensor outputs and oxygen concentrations and ambient gas pressures related to the oxygen sensor output; and computing a set of fitted coefficients corresponding to the calibration curve based on the measured oxygen sensor outputs and the related oxygen concentrations and ambient gas pressures; and wherein the microprocessor receives data from the oxygen sensor associated with the measured oxygen outputs and data from the pressure sensor comprising a measured ambient gas pressure, and calculates the oxygen concentration by applying the ambient gas pressure data and oxygen sensor outputs as variables to the calibrated oxygen concentration data received from the memory.

5. The system of claim 1, wherein the microprocessor is further configured to generate calibrated oxygen response data based on at least one of a duration of use of the oxygen sensor and an age of the oxygen sensor.

6. The system of claim 1, wherein the microprocessor is further configured to determine ambient $CO_2$ levels based on a change between the temperature independent oxygen level and a recorded nominal oxygen level.

7. An oxygen sensing system, the system comprising:

an oxygen sensor for detecting an oxygen level in an ambient gas environment;

a non-oxygen active environmental reference sensor configured to sense one or more environmental factors that is not responsive to ambient oxygen levels;

a microprocessor for receiving a signal from the oxygen sensor corresponding to the detected oxygen level and from the non-oxygen active environmental sensor corresponding to the one or more environmental factors; and a memory for storing data comprised of calibrated reference sensor response formulas corresponding to a plurality of non-active sensor outputs for one or more ambient environmental conditions and a corresponding output of the active oxygen sensor; and wherein the microprocessor calculates an environment independent oxygen level utilizing the signals from the oxygen sensor and the non-oxygen active environmental sensor as inputs for the stored calibration formulas.

8. The system of claim 7, wherein the microprocessor is further configured to generate calibrated oxygen response formulas based on at least one of a duration of use of the oxygen sensor and an age of the oxygen sensor.

9. The system of claim 7, wherein the microprocessor is further configured to determine ambient $CO_2$ levels based on a change between the detected oxygen level and a recorded nominal oxygen level.

10. The system of claim 7, wherein the signal from the non-oxygen active environmental sensor comprises a voltage output that is not responsive to ambient oxygen levels and the signal from the oxygen sensor is responsive to ambient oxygen levels.

11. A method for determining an oxygen level utilizing an oxygen sensing system, the method comprising:

detecting an oxygen level in an ambient gas environment utilizing an oxygen sensor;

measuring a temperature of the ambient gas environment utilizing a temperature sensor;

receiving the detected oxygen level and the measured temperature at a microprocessor coupled to the oxygen sensor and the temperature sensor;

retrieving calibrated temperature response data corresponding to a plurality of oxygen gas concentrations at a plurality of temperatures stored in a memory utilizing the microprocessor; and dynamically adjusting the detected oxygen level based on the measured temperature by utilizing the microprocessor to compare the detected oxygen level with the calibrated temperature response data and to determine a temperature independent oxygen level based on the comparison.

12. The method of claim 11, further comprising amplifying a difference between the baseline voltage and a sensed voltage corresponding to the detected oxygen level utilizing a baseline amplifier.

13. The method of claim 11, wherein the calibrated temperature response data is generated by:
  measuring oxygen sensor outputs for a plurality of oxygen concentrations at a plurality of ambient gas temperatures;
  measuring temperature sensor outputs for the plurality of ambient gas temperatures;
  determining a best fit calibration equation by approximating a calibration curve with a multi-variant fit based on the oxygen sensor outputs and oxygen concentrations and ambient gas temperatures related to the oxygen sensor output; and
  computing a set of fitted coefficients corresponding to the calibration curve based on the measured oxygen sensor outputs and the related oxygen concentrations and ambient gas temperatures; and
  wherein the microprocessor receives data from the oxygen sensor associated with the measured oxygen outputs and data from the temperature sensor comprising a measured ambient gas temperature, and calculates the oxygen concentration by applying the ambient gas temperature data and oxygen sensor outputs as variables to the calibrated oxygen concentration data received from the memory.

14. The method of claim 11, further comprising:
  detecting an ambient gas pressure utilizing a pressure sensor for detecting an ambient gas pressure, wherein the stored calibration data is generated by:
  measuring oxygen sensor outputs for a plurality of oxygen concentrations at a plurality of ambient gas pressures;
  measuring pressure sensor outputs for the plurality of ambient gas pressures;
  determining a best fit calibration equation by approximating a calibration curve with a multi-variant fit based on the oxygen sensor outputs and oxygen concentrations and ambient gas pressures related to the oxygen sensor output; and
  computing a set of fitted coefficients corresponding to the calibration curve based on the measured oxygen sensor outputs and the related oxygen concentrations and ambient gas pressures; and
  wherein the microprocessor receives data from the oxygen sensor associated with the measured oxygen outputs and data from the pressure sensor comprising a measured ambient gas pressure, and calculates the oxygen concentration by applying the ambient gas pressure data and oxygen sensor outputs as variables to the calibrated oxygen concentration data received from the memory.

15. The system of claim 11, further comprising generating calibrated oxygen response data based on at least one of a duration of use of the oxygen sensor and an age of the oxygen sensor utilizing the microprocessor.

16. The system of claim 11, further comprising determining ambient CO2 levels based on a change between the temperature independent oxygen level and a recorded nominal oxygen level utilizing the microprocessor.

17. A method for determining an oxygen level utilizing an oxygen sensing system, the method comprising:
  detecting an oxygen level in an ambient gas environment utilizing an oxygen sensor;
  sensing one or more environmental factors that is not responsive to ambient oxygen levels utilizing a non-oxygen active environmental reference sensor;
  receiving at a microprocessor a signal from the oxygen sensor corresponding to the detected oxygen level and from the non-oxygen active environmental sensor corresponding to the one or more environmental factors;
  utilizing the microprocessor to retrieve from a memory calibrated data corresponding to a plurality of non-active sensor outputs for one or more ambient environmental conditions and a corresponding output of the active oxygen sensor; and
  utilizing the microprocessor to calculate an environment independent oxygen level utilizing the signals from the oxygen sensor and the non-oxygen active environmental sensor as inputs for the stored calibration data.

18. The method of claim 17, further comprising generating calibrated oxygen response formulas based on at least one of a duration of use of the oxygen sensor and an age of the oxygen sensor utilizing the microprocessor.

19. The method of claim 17, further comprising determining ambient CO2 levels based on a change between the detected oxygen level and a recorded nominal oxygen level utilizing the microprocessor.

* * * * *